United States Patent [19]

Violante et al.

[11] Patent Number: 4,997,454

[45] Date of Patent: Mar. 5, 1991

[54] METHOD FOR MAKING UNIFORMLY-SIZED PARTICLES FROM INSOLUBLE COMPOUNDS

[75] Inventors: Michael R. Violante, Rochester; Harry W. Fischer, Pittsford, both of N.Y.

[73] Assignee: The University of Rochester, Rochester, N.Y.

[21] Appl. No.: 343,761

[22] Filed: Apr. 26, 1989

Related U.S. Application Data

[63] Continuation-in-part of Ser. No. 735,459, May 17, 1989, Pat. No. 4,826,689, which is a continuation-in-part of Ser. No. 612,725, May 21, 1984.

[51] Int. Cl.$^5$ .............................................. C01F 7/34
[52] U.S. Cl. ................................. 23/305 A; 210/639; 210/709; 210/729; 264/9; 424/489; 424/492; 502/8; 423/495; 514/410; 514/951; 514/965
[58] Field of Search ............. 23/305 A; 210/634, 702, 210/709, 710, 729, 737, 738, 768, 772, 773, 749, 96.1, 639; 264/9; 424/489, 490, 492, 497; 502/8; 514/228.2, 410, 951, 965; 423/462, 495, 605, 632

[56] References Cited

U.S. PATENT DOCUMENTS

| | | | |
|---|---|---|---|
| 2,340,672 | 2/1944 | Lister | 210/634 |
| 2,776,241 | 1/1957 | Priewe et al. | 167/95 |
| 2,861,024 | 11/1958 | Silver | 167/65 |
| 2,919,181 | 12/1959 | Reinhardt | 55/22 |
| 3,393,055 | 7/1968 | Stevenson | 210/738 |
| 3,415,747 | 12/1960 | Glew | 210/729 |
| 3,489,686 | 1/1970 | Parran | 252/106 |
| 3,534,116 | 10/1970 | Fuller | 210/634 |
| 3,580,853 | 5/1971 | Parran | 252/152 |
| 3,594,313 | 7/1971 | Carlson | 210/709 |
| 3,663,685 | 5/1972 | Evans | 424/1 |
| 3,723,325 | 3/1973 | Parran | 252/106 |
| 3,753,916 | 8/1973 | Parran | 252/107 |
| 3,761,417 | 9/1973 | Parran | 252/106 |
| 3,761,418 | 9/1973 | Parran | 252/106 |

(List continued on next page.)

FOREIGN PATENT DOCUMENTS

| | | |
|---|---|---|
| 0169618 | 1/1986 | European Pat. Off. . |
| 0300828 | 1/1989 | European Pat. Off. . |
| 3742473A1 | 7/1988 | Fed. Rep. of Germany . |
| WO86/02002 | 4/1986 | PCT Int'l Appl. . |
| 867650 | 5/1961 | United Kingdom . |
| 2200048 | 7/1988 | United Kingdom . |

OTHER PUBLICATIONS

Violante et al., "Biodistribution of a Particulate Hepatolienographic CT Contrast Agent," Inv. Radiol. 16: 40 (1981).

Lauteala et al., "Effect of Intravenously Administered Iodipamide Ethyl Ester Particles on Rat Liver Morphology," Inv. Radiol. 19: 133 (Mar.-Apr. 1984).

Violante et al., "Protein Binding to Iothalamate Ethyl Ester," Inv. Radiol. 14: 177 (1979).

Violante et al., "Maximizing Hepatic Contrast Enhancement with a Particulate Contrast Agent in Computed Tomography."

Violante and Fischer, "Particulate Suspensions as Contrast Media," ch. 13 in *Handbook of Experimental Pharmacology*, vol. 73, Sovak, ed. (Springer Berlin, 1984).

(List continued on next page.)

*Primary Examiner*—Peter Hruskoci
*Attorney, Agent, or Firm*—Kenyon & Kenyon

[57] ABSTRACT

The invention involves a method for making uniformly sized particles from solid compounds. First, a suitable solid compound is dissolved in a suitable solvent. Then, a precipitating liquid is infused, precipitating non-aggregated particles with substantially uniform mean diameter. The particles are then separated from the solvent. Depending on the solid compound and the desired particle size, the parameters of temperature, ratio of non-solvent to solvent, infusion rate, stir rate, and volume can be varied according to the invention. The precipitating liquid may be aqueous or non-aqueous, depending upon the relative solubility of the compound and the desired suspending vehicle.

22 Claims, 6 Drawing Sheets

U.S. PATENT DOCUMENTS

| | | | |
|---|---|---|---|
| 3,875,071 | 4/1975 | Grand | 252/106 |
| 3,887,692 | 6/1975 | Gilman | 423/495 |
| 3,892,800 | 7/1975 | Nickel et al. | 424/1 |
| 3,919,190 | 11/1975 | Barker et al. | 424/180 |
| 3,957,741 | 5/1976 | Rembaum et al. | 526/312 |
| 3,979,520 | 9/1976 | Rothe et al. | 424/321 |
| 4,005,188 | 1/1977 | Tilly et al. | 424/5 |
| 4,009,232 | 2/1977 | Shiiki et al. | 264/9 |
| 4,059,624 | 11/1977 | Harrison | 260/404.5 |
| 4,105,598 | 8/1978 | Yen et al. | 521/53 |
| 4,180,619 | 12/1979 | Makhlouf et al. | 526/202 |
| 4,215,994 | 8/1980 | Kodras | 210/634 |
| 4,234,600 | 11/1980 | Sirrenberg et al. | 424/310 |
| 4,356,108 | 10/1982 | Schwab | 252/316 |
| 4,356,109 | 10/1982 | Saeki et al. | 252/316 |
| 4,395,391 | 7/1983 | Pfeiffer et al. | 424/5 |
| 4,406,878 | 9/1983 | DeBoer | 424/5 |
| 4,426,291 | 1/1984 | Sharangpani et al. | 210/634 |
| 4,492,720 | 1/1985 | Mosier | 427/213.3 |
| 4,515,695 | 5/1985 | Knopp, Jr. | 210/634 |
| 4,532,183 | 7/1985 | Shackle | 428/402.22 |
| 4,594,371 | 6/1986 | Nauman | 523/340 |
| 4,670,461 | 6/1987 | Haugwitz et al. | 514/410 |
| 4,783,484 | 11/1988 | Violante et al. | 514/858 |
| 4,803,202 | 2/1989 | Haugwitz et al. | 514/228.2 |
| 4,826,689 | 5/1989 | Violante et al. | 210/709 |

OTHER PUBLICATIONS

Grimes et al., "Formulation and Evolution of Ethiodized Oil Emulsion for Intravenous Hepatography," *J. Pharmaceut. Sci. 68: 52 (1979).*

Klebanoff, "Myeloperoxidase-Halide-Hydrogen Peroxide Antibacterial System," *J. Bacteriol.*, 95: 2131 (1968).

Woeber et al., "Stimulation by Phagocytosis of the Deiodination of L-Thyroxine in Human Leukocytes," *Science*, 176: 1039 (1972).

Steigbigel et al., "Phagocytic and Bactericidal Properties of Normal Human Monocytes" *J. Clin. Invest.*, 53: 131 (1974).

DeChatelet et al., "Effect of Phorbol Myristate Acetate on the Oxidative Metabolism of Human Polymorphonuclear Leukocytes," Blood, 47: 545 (1976).

Violante et al., "Particulate Contrast Media," Invest. Radiol., 15: S329 (1980).

Violante et al., "Biodistribution of a Particulate Hepatolienograph CT Contrast Agent: A Study of Iodipamide Ethyl Ester in the Rat," Invest. Radiol., 16: 40 (1981).

Kelbanoff, "Iodination with Bacteria: a Bacterial Mechanism", J. Exp. Med. 126: 1063-1078 (1967).

Fischer, "Improvement in Radiographic Contrast Media Through the Development of Colloidal or Particulate Media: An Analysis," *J. Theor. Biol.* 67: 653-670 (1977).

Violante et al., "Particulate Contrast Media for Computed Tomographic Scanning of the Liver," *Inv. Radiol.* 15: S171 (1980).

Pullman, Violante, and Steigbigel, "Enhancement of Phagocyte Intracellular (ic) Killing by Iodipamide Ethyl Ester," Abstract, ASM Meeting, Oct. 8, 1984.

METHOD FOR MAKING UNIFORMLY-SIZED PARTICLES FROM INSOLUBLE COMPOUNDS

BACKGROUND OF THE INVENTION

This is a continuation-in-part application of Ser. No. 735,459, filed May 17, 1985 now U.S. Pat. No. 4,826,689 which is a continuation-in-part of Ser. No. 612,725, filed May 21, 1984.

Particles of compounds having low solubility in a dispersing medium are commonly used in a wide variety of applications, including pharmaceuticals, ceramics, paints, inks, dyes, lubricants, pesticides, insecticides, fungicides, fertilizers, chromatography columns, cosmetics, lotions, ointments, and detergents. Aqueous dispersions of particles are used in many cases to avoid hazards such as flammability and toxicity associated with organic solvents. Such dispersions typically have a broad range of particle size.

In many cases product performance is improved by controlling the particle size distribution. In general, smaller particles of a compound provide a more uniform dispersion and will dissolve faster than larger particles of the same compounds. Control of particle size is, therefore, important in controlling the rate of solubilization.

Many drugs have been formulated as particles for sustained-release following oral, aerosol, subcutaneous, intramuscular, or other routes of administration. Particle size is one important factor affecting the release rate of these drugs. Those skilled in the art can discern other examples for using particle size to control product performance for the substances listed above.

Drugs that are insoluble in water can have significant benefits when formulated as a stable suspension of particles of less than three microns diameter. In this particulate form, the drug can be injected intravenously, circulate in blood, and be preferentially accumulated in, for example, the reticuloendothelial system, where it can facilitate normal reticuloendothelial functions such as detoxification. Alternatively, the drug can reside in the reticuloendothelial cells where it is stored until solubilized or metabolized into an active form which circulates in blood to other tissues for efficacy. This "slow" release of active drug can provide more constant drug concentrations in plasma over a period of hours, days, weeks, or months, resulting in improved therapeutic efficacy. Biodegradable particles which are radiopaque or labelled with a radioisotope are useful for diagnostic imaging of organs, such as liver and spleen, with high concentrations of fixed reticuloendothelial function.

Many advantages have already been recognized for insoluble particulate radiopaque contrast media, for example, as explained in "Improvement in Radiographic Contrast Media Through the Development of Colloidal or Particulate Media: an Analysis", by Harry W. Fischer, *Journal of Theoretical Biology*, 67: 653–670 (1977). More recent papers on this subject include Violante, M. R., Fischer, H. W., and Mahoney, J. A., "Particulate Contrast Media," *Invest. Radiol.*, 15: S329 November-December 1980; and Violante, M. R., Dean, P. B., Fischer, H. W., and Mahoney, J. A., "Particulate Contrast Media for Computer Tomographic Scanning of the Liver", *Invest. Radiol.*, 15: 171 November-December 1980.

There are enormous medical implications for the intravenous administration of drugs formulated as suspensions of particles of three microns diameter, or less, which can be accumulated by phagocytic cells and slowly solubilized for sustained release into plasma for circulation to other organs and tissues. Obvious drug classes appropriate for formulation as particulate suspensions include: antineoplastics, antimicrobials, antivirals, anticoagulants, antihypertensives, antihistamines, antimalarials, male and female contraceptives, antiepileptics, depressants and antidepressants, adrenocortical steroids, hormones and hormone antagonists, cardiac glycosides, immunosuppressants, beta-blockers, water-insoluble vitamins, sympathomimetics, hypoglycemic agents, hyperglycemic agents, analgesics, tranquilizers, mood altering drugs, and others. The treatment of deficiency diseases, alcohol abuse, drug abuse, and many others could be improved with intravenous administration of particulate suspensions of the appropriate drug. Other medical applications for particulate drug suspensions will be apparent to those skilled in the art.

Accurate control of particle size is essential for safe and efficacious use of these formulations. Particles must be less than three microns in diameter to safely pass through capillaries without causing emboli. This is critical for intravenous administration since the particles must pass through lung capillaries before reaching the fixed reticuloendothelial cells of liver and spleen. Restriction to particle diameters of 0 01–0.1 micron could result in selective accumulation of these particles in certain tissues, e.g., neoplastic tissue, where capillaries are somewhat more porous than capillaries of normal tissues. Suspensions of particles with diameters greater than 10 microns could be useful for selective intra-arterial administration to purposely embolize vessels feeding abnormal tissue such as a neoplasm. Accurate and precise control of particle diameters is essential for efficacy while minimizing or avoiding adverse effects in each of these applications.

Conventional methods of making insoluble compounds produce particles of many different sizes, many of which are unsuitable for the purpose at hand. Mechanically sorting or separating a desired particle size from a mix of sizes is difficult and unsatisfactory. Centrifuging and filtration do not produce high yields of particles that are all precisely the same desired size.

Investigations of water-insoluble radiopaque contrast materials required uniform particles in specific sizes that were very difficult to obtain by conventional methods. Precipitation as a way of directly forming particles of a predetermined size was then investigated. Partial success was achieved with one material and one method as reported in "Particulate Contrast Media", *Investigative Radiology*, 15: S329 November-December 1980; but this method would not work With other materials and would not allow accurate variation and control of the particle size produced.

Further investigation led to the invention of this application, which is effective with any compound having a solubility in a given liquid of preferably less than one part per ten thousand to obtain a predetermined particle size of the compound in a dispersion.

SUMMARY OF THE INVENTION

The invention involves a method of making uniformly sized particles of a solid compound by, first preparing a solution of the solid compound in a suitable solvent for the compound, second, infusing a precipitating liquid into the solution at a temperature between about $-50°$ C. and about $100°$ C. and at an infusion rate of from about 0.01 ml per minute to about 3000 ml per minute per unit volume of 50 ml, the solid compound having essentially little solubility in the precipitating liquid and the solvent being miscible in the precipitating liquid, so as to produce a suspension of precipitated solid compound in the form of substantially nonaggregated particles with a substantially uniform mean particle diameter selected from the range of up to about 10 microns, such that the particle size is directly related to the solution temperature and inversely related to infusion rate, and then separating the particles from the solvent and washing in a suitable washing liquid.

In preferred embodiments of the invention, additional precipitating liquid is added to the suspension before the particles are separated from the solvent. Separation can be accomplished, for example by centrifugation, membrane filtration, reverse osmosis, or other methods.

The mean particle diameter of the particles can be up to about 10 microns preferably in a range of 0.01 microns to about 5 microns.

Particles made according to this invention will typically have a particle size distribution with a maximum relative standard deviation of 30%, for example 95% of the particle having a mean size of 1.0 micron will be within the size range of 0.5 to 1.5 microns.

The present invention is useful for compounds which preferably have essentially little solubility in a precipitating liquid, i.e. a solubility of less than about one part per ten thousand in the precipitating liquid. Generally, any compound that meets the other requirements of the invention is suitable, including many drugs. The compound may be organic or inorganic.

The solvent may be organic or inorganic, as long as the solubility of the compound in the solvent is greater than about 10 mg/ml. Also, the solvent must be miscible with the precipitating liquid.

The washing liquid can be the same as or different than the precipitating liquid. In certain instances it may be advantageous for the compound to have a lower solubility in the washing liquid than in the precipitating liquid in order to maximize yield.

When the solid compound has essentially little aqueous solubility, the precipitating liquid can be water, a solution of a mineral salt, a surfactant solution, or an organic solvent in which the compound is poorly soluble. Suitable aqueous surfactant solutions include 5% polyvinylpyrrolidone C-30, 0.1% polyvinylpyrrolidone C-15, 0.1% human serum albumin, 0.1% pluronic F-68 (poloxamer 188), and 0.33% gelatin, alone or combined with 0.6% hetastarch, 0.02% propylene glycol, or 2% sucrose. The organic solvent can be dimethyl sulfoxide, dimethyl formamide, N,N'-dimethyl acetamide, phenol, isopropanol, or other solvents.

In one embodiment of the invention, the solid compound has poor aqueous solubility, i.e. an aqueous solubility from about one part per ten thousand to about one part per one hundred. This embodiment is particularly suitable for situations where a compound which might normally be considered water-insoluble encounters a significant yield loss when precipitated in an aqueous solution. In order to improve yield, a precipitating and washing liquid may be chosen in which the compound is even less soluble than water. In this embodiment, the solvents which may be used include the organic solvents previously identified among others. However, the precipitating liquid is at least substantially non-aqueous. Suitable non-aqueous solutions include alcohols such as ethanol, and alcoholic surfactant solutions such as 1% (w/v) polyvinylpyrrolidone in ethanol, other lower aliphatic alcohols, acids, amides, aldehydes, ketones, and glycols.

In one embodiment, the method includes the additional step of diluting the solution in which the compound is dissolved with a non-solvent, i.e. a liquid in which the compound is poorly soluble but does not cause the compound to precipitate, such that the ratio of non-solvent to solvent is between about 100:1 and about 1:100, after preparing the solution and before the infusion step, so that the particle size is directly related to the ratio of non-solvent to solvent.

In one preferred embodiment the solid compound is iodipamide ethyl ester, an ethyl ester of a triiodobenzoio acid derivative, and is dissolved in dimethyl sulfoxide and diluted with ethanol. The compound is thereafter precipitated with an aqueous surfactant solution. If the ratio of ethanol to dimethyl sulfoxide is greater than about two, the mean particle diameter is greater than about one micron, and if the ratio of ethanol to dimethyl sulfoxide is less than about two, the mean particle diameter is less than about one micron.

In another preferred embodiment, the solid compound is mitindomide, an anticancer drug having the molecular formula $C_{14}H_{12}N_2O_4$ and a molecular weight of 272.3. The mitindomide is dissolved in dimethyl sulfoxide and the precipitating liquid used is 1% (w/v) polyvinylpyrrolidone in 99% ethanol.

In yet another preferred embodiment the solid compound is aluminum chloride hexahydrate. It is dissolved in ethanol (99%), and thereafter diluted with acetone. The compound is then precipitated with an aqueous surfactant solution.

DETAILED DESCRIPTION OF THE INVENTION

This invention concerns the preparation of uniform particles of a predetermined size. One aspect of the invention concerns the preparation of uniform particles of a predetermined size in a vehicle in which the concentration of the compound in the vehicle is greater than the solubility of the compound in that vehicle. The particles are formed by a carefully controlled precipitation of the compound into a suitable precipitating liquid from a solvent in which the compound is soluble.

Figure 1:
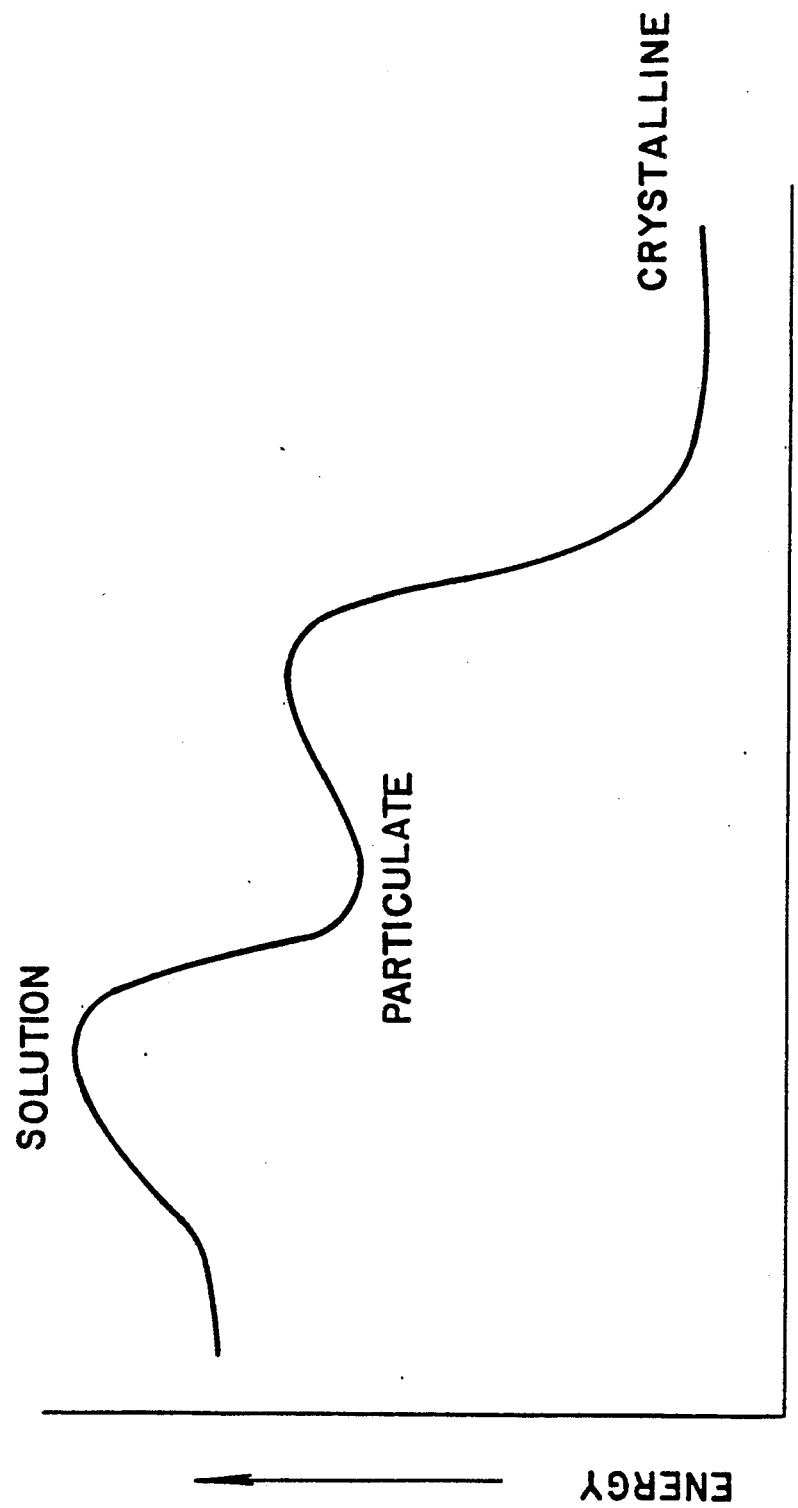
FIG. 1 is a graph of free energy of the various phases of the compounds used in the invention.
Figure 2:
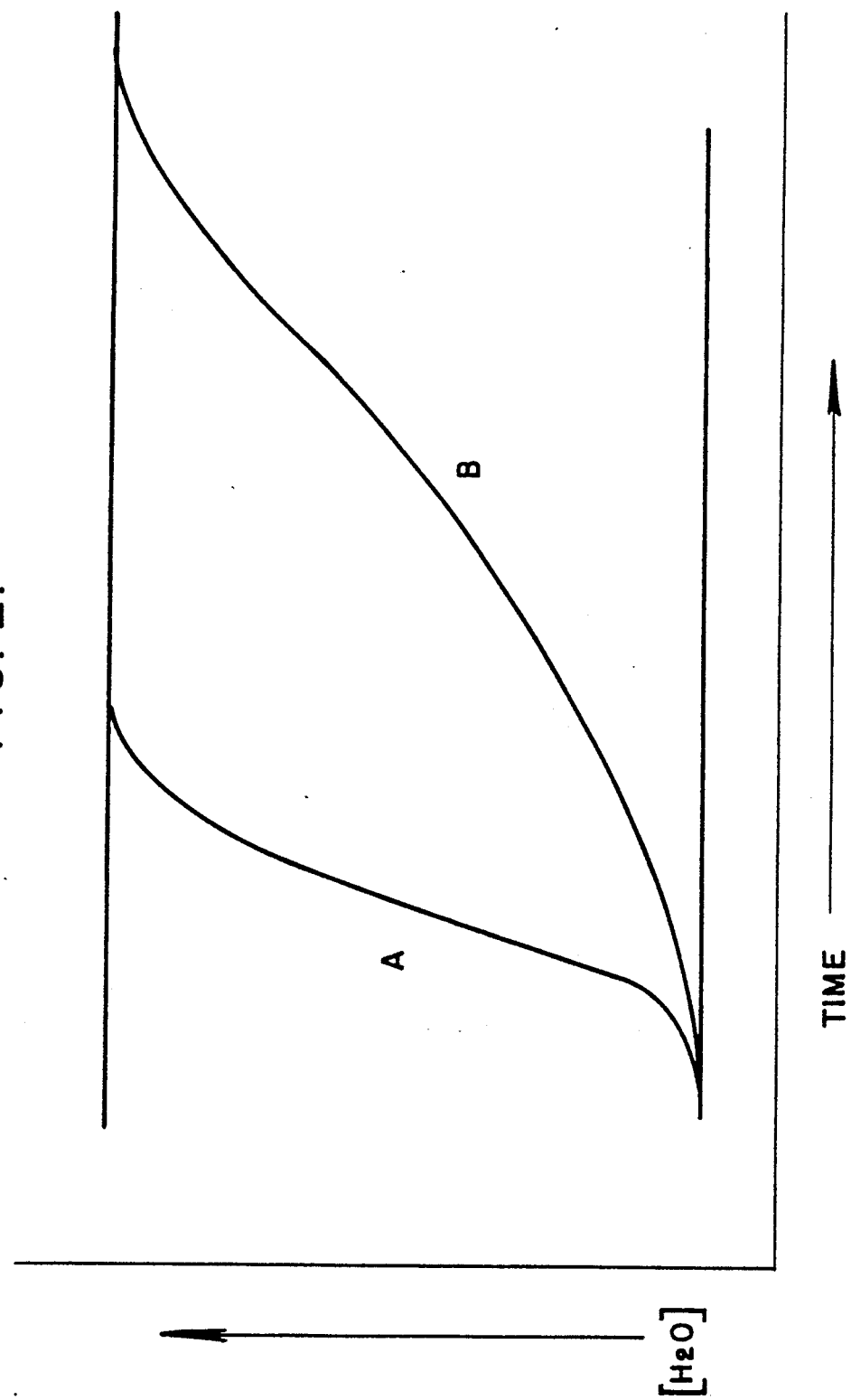
FIG. 2 is a graph of the relationship between size distribution of particles and time interval between onset and completion of precipitation.

The physical chemical principles thought to be involved in this invention are demonstrated in FIGS. 1 and 2. FIG. 1 shows that the free energy of the system is higher when the compound is dissolved in the organic solvent than when the compound exists in the particulate or crystalline state. During precipitation the compound will naturally convert to the crystalline form—the lowest free energy state—unless it is trapped in the metastable particulate form, a condition where its free energy is intermediate between the solution and the crystalline phases. When properly practiced, this invention enables the trapping of a compound in the metastable particle state, precluding transformation to the crystalline state.

The size distribution of particles formed during precipitation can be correlated with the time interval between onset and completion of precipitation. As shown in FIG. 2, a very short time interval results in the production of uniformly sized particles (A), while a very long time interval results in a broad particle size distribution (B). Intermediate conditions produce intermediate particle size distributions.

An important parameter for utilization of this invention is the solubility of the compound in the precipitating liquid. Thus, compounds having essentially little aqueous solubility, i.e. compounds which have an aqueous solubility of less than one part in ten thousand, may be precipitated in an aqueous solution in order to obtain an excellent yield. Compounds which are more water-soluble can also use an aqueous precipitating liquid. However, the higher the solubility of the compound, the greater the probability that some of the compound will dissolve in the aqueous phase and transform to the more stable crystalline state. Also, redissolution in the aqueous phase can lead to a broadening of the particle size distribution. For these reasons, it is preferred that an aqueous precipitating liquid be used for compounds having a water-solubility of less than one part in ten thousand.

It has been found that it is possible to prepare suspensions of compounds which are poorly soluble in aqueous solutions, i.e., have a solubility from about one part per ten thousand to about one part per one hundred which provide excellent yields by using an acceptable precipitating liquid in which the compounds have even less solubility than water. The difference in the solubility of the compound in water as compared to the precipitating liquid need not be large in order to be significant in terms of yield. In order to make particles of a uniform and predetermined size, a solution of the solid compound in a suitable solvent is prepared. The solution may be diluted with a non-solvent that does not cause the drug or other compound to precipitate. A precipitating liquid is also prepared, preferably with a surfactant, in sufficient quantity to both precipitate the drug or other compound and stabilize the resulting suspension of particles of the compound against aggregation. The precipitating liquid may be used alone when compounds which do not aggregate are used. The precipitating liquid is infused into the solution in which the compound is dissolved under carefully controlled conditions, including: the rate of stirring of the organic solution, the rate of infusion of the aqueous solution, the volume of the organic solution and the temperature of the solutions and the suspension. The precipitating liquid may be infused, for example, through a needle of standard guage.

In investigations of varying parameters to adjust for particle size, three usable relationships were discovered: (1) diluting the solution with more of the non-solvent produces larger particles, and diluting with less of the non-solvent produces smaller particles; (2) higher temperatures of the solution during precipitation produce larger particles, and lower temperatures of the solution during precipitation produce smaller particles; and (3) at a given stirring rate of the organic solution, faster infusion rates of precipitating liquid produce smaller particles while slower infusion rates produce larger particles.

When the precipitation is complete, the uniformly sized particles are washed to remove the solvent, i.e. by centrifugation, filtration, etc. In most cases, the particles should be separated from the solvent quickly to prevent transformation to a crystalline form.

Aqueous precipitating liquids are useful for many compounds, including but not limited to organic compounds such as iodipamide ethyl ester, iothalamate ethyl ester, iosefamate ethyl ester, 2,2', 4 4'-tetrahydroxybenzophenone, RS nitrocellulose, progesterone, beta-2,4,6-triiodo-3-dimethyl formamidinophenyl propionic acid ethyl ester, isopropylpyrrolizine derivative (NSC-278214), N-(trifluoroacetyl) Adrimycin 14 valerate, 1,2 diaminocyclohexane malinate platinum (II), norethisterone, acetyl salicylic acid, wafarin, heparin-tridodecyl methyl ammonium chloride complex, sulfamethoxazole, cephalexin, prednisolone acetate, diazepam, clonazepam, methidone, naloxone, disulfiram, mercaptopurine, digitoxin, primaguine, mefloquine, atropine, scopolamine, thiazide, furosemide, propanalol, methyl methacrylate, poly methyl methacrylate, 5-fluorodeoxyuridine, cytosine arabinoside, acyclovir, and levonorgestrel; and inorganic compounds such as aluminum chloride hexahydrate, the oxides of iron, copper, manganese, tin.

Compounds which are better suited for precipitation using a non-aqueous precipitating liquid include organic compounds such as mitindomide, hydrolytically unstable compounds such as isopropylpyrrolizine (IPP, or carbamic acid, (1-methylethyol)-, (5-(3,4-dichlorophenol)-2,3-dihydro-1,H-pyrrolizine-6,7-diyl) bis(methylene ester); and inorganic compounds such as iron citrate, iron iodate, calcium pyrophosphate, calcium salicylate, platinum dichloride and sodium pyrophosphate.

The first step is to prepare a solution of the compound of interest in a suitable solvent for that compound. This can occur as the compound is synthesized as a dissolved solid, or it can be done by simply dissolving the compound in the solvent of choice.

The solvent is chosen to suit the compound. For example, dimethylformamide (DMF) is a solvent for iothalamate ethyl ester (IEE) and iosefamate ethyl ester (IFE), and dimethylsulfoxide (DMSO) is a solvent for iodipamide ethyl ester (IDE) and IEE. DMSO is also a suitable solvent for compounds such as mitindomide. Another suitable solvent for many compounds, and especially IPP, is tetrahydrofuran (THF).

The solution is then optionally diluted with a non-solvent that does not cause the compound to precipitate. The non-solvent causes greater dispersion of the dissolved molecules of the compound in the liquid phase. Greater dilution of the solution with non-solvent produces larger particles, and less dilution of the solution with non-solvent produces smaller particles.

The non-solvent should not precipitate the compound when it is added to the solution. Lower aliphatic alcohols, such as ethanol, are effective non-solvents for solutions of IDE and IEE in DMSO. For the ethyl esters of triiodobenzoic acid, proportions of non-solvent to solvent at a ratio of 2 or more can produce 1 to 3 micron sized particles (depending on other parameters); and ratios of less than 2 can produce submicron particles, at least as applied to DMSO solutions diluted with ethanol.

To precipitate the compound from the solution in a desired particle size, a solution of a surfactant is prepared in sufficient quantity to effect complete precipitation of the compound and to stabilize the resulting suspension of particles of the compound against aggregation. The surfactant provides the stabilization against aggregation, while a suitable precipitating agent causes the precipitation of the compound. Presence of extra surfactant solution is advisable to ensure stabilization so that precipitated particles suspended in liquid do not aggregate, forming agglomerates of an improperly large size. While surfactants are used in most cases, some compounds appear to form stable, substantially non-aggregated particles without the use of surfactants. Examples of such non-aggregrating compounds are certain heparin complexes.

It is thought that particles with relatively high surface charge are less likely to require surfactant in the precipitating solution. The surface charge of a particle is sometimes referred to as its zeta potential, a measurement of charge which falls off with distance. There may be a threshold zeta potential above which no surfactant is needed, but below which, surfactant is needed to keep the precipitating particles from aggregating. The zeta potential is directly correlated with the polarity or net charge of a compound. Thus, the need for surfactant in the precipitating solution may be predicted from the extent of the charge or polarity of the compound employed in the method of the invention. For example, heparin complexes are highly charged, and form stable non-aggregated particles when precipitated with water.

Generally, such a theory notwithstanding, empirical methods will suffice; that is, a precipitation may first be performed with water, and if aggregation occurs, then a precipitation in the presence of surfactant is indicated. Surfactants are chosen for their compatibility with the compound and their ability to stabilize a suspension of compound particles. For work with IEE and IDE drugs, a solution of 5% polyvinylpyrrolidone (C-30), 0.1% polyvinylpyrrolidone (C-15), or 0.1% human serum albumin is preferred. Also 0.1% Pluronic F-68, [Poloxamer 188, a poly(oxyethylene-co-oxypropylene) polymer], a 0.33% gelatin, 0.33% gelatin plus 0.6% Hetastarch, 0.33% gelatin plus 0.002% propylene glycol, and 0.33% gelatin plus 2% sucrose, or other surfactants known to one skilled in the art can be used.

To precipitate particles of the compound in the desired sizes, the precipitating liquid and the solution are combined under controlled conditions of temperature, ratio of infusion rate to stirring rate, and the proportion of non-solvent to solvent in the dispersed solution.

Preferably, the solution being infused with precipitating liquid is agitated. This can be accomplished by stirring, shaking, by the infusion itself and by other techniques known to those skilled in the art. This effect can also be achieved by combining a stream of precipitating liquid with a stream of the solution.

The precipitation of the compound occurs exothermically, heating the solution and the resulting suspension. The temperature of the solution and resulting suspension is controlled to achieve the particle size of precipitate that is desired. Higher solution temperatures during precipitation produce larger particles, and lower solution temperatures during precipitation produce smaller particles. Since many compounds are less soluble at lower temperatures, it is generally preferred to conduct the infusion of precipitating liquid at a low temperature in order to maximize yield. The lower limit of the temperature at which precipitation can be conducted is, of course dependent upon the freezing point of the solvent, precipitating liquid, as well as economic concerns.

Also, faster infusion rates at constant stirring rate of organic solution produce smaller particles, and slower infusion rates produce larger particles.

Figure 3:
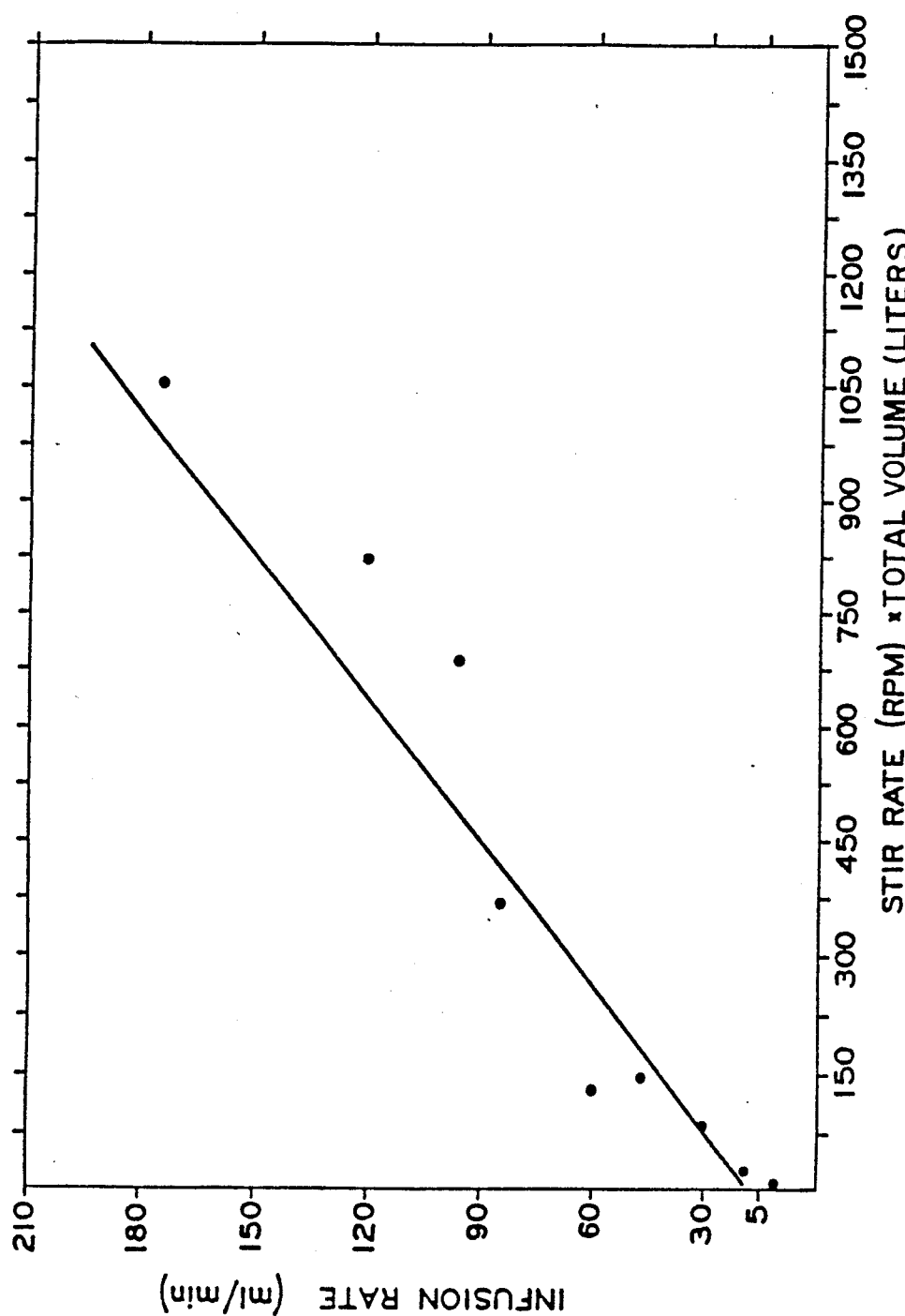
FIG. 3 is a graph of infusion rate (ml/min.) (of aqueous precipitating liquid) as a function of the product of stir rate (rpm) and total volume (liters) of the organic solution at a constant temperature; the relationship: aqueous infusion rate (ml/min.)=23+0.14 [stir rate (rpm)×volume organic solution (1)] defines the parameters for production of iodipamide ethyl ester particles of one micron diameter at a constant temperature (4° C.) and in dimethyl sulfoxide/ethanol.
Figure 4:
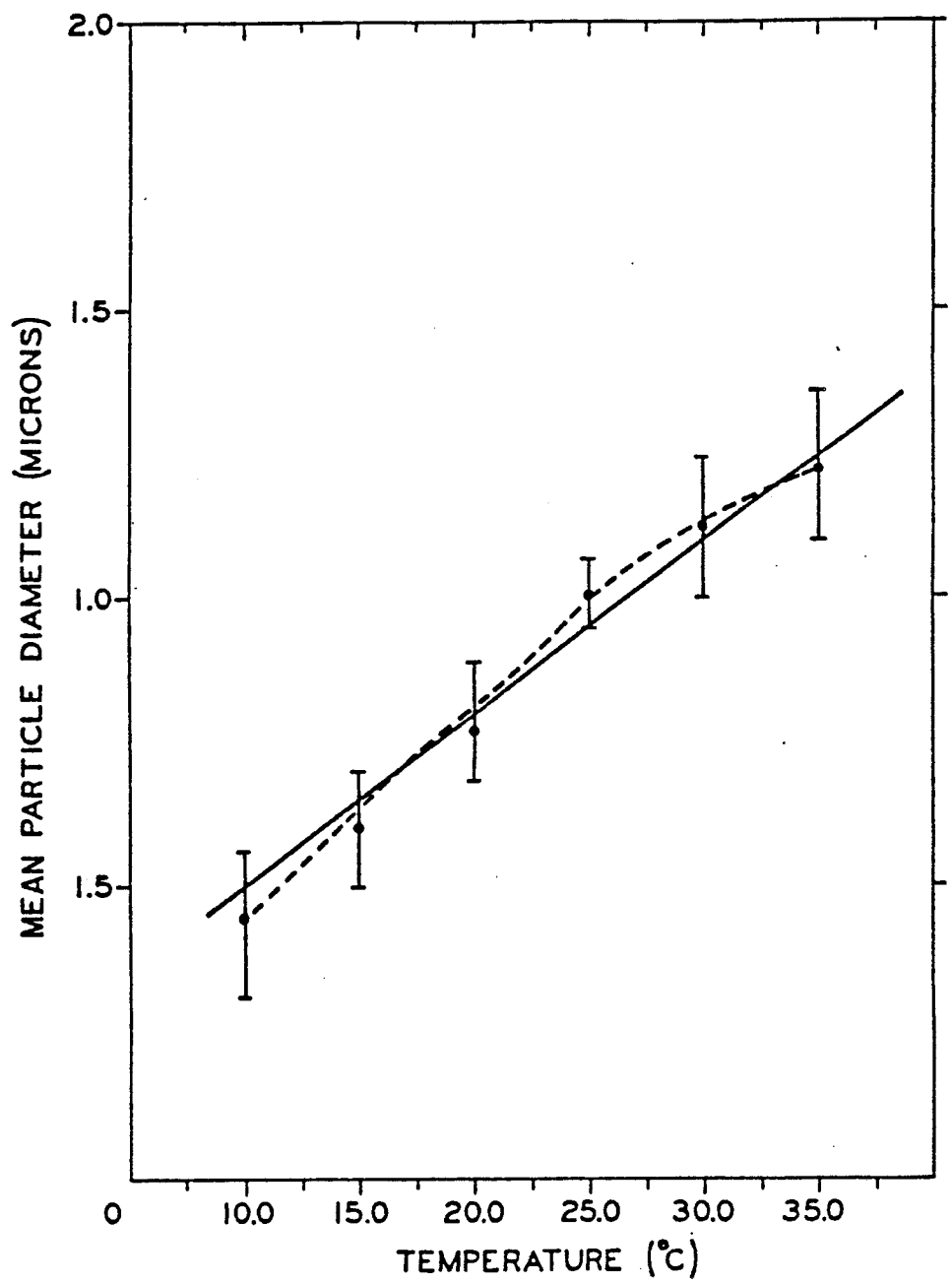
FIG. 4 is a graph showing iodipamide ethyl ester particle size as a function of temperature at a constant ratio of infusion rate of aqueous precipitating liquid to [stir rate (rpm)×volume of organic solution]
Figure 5:
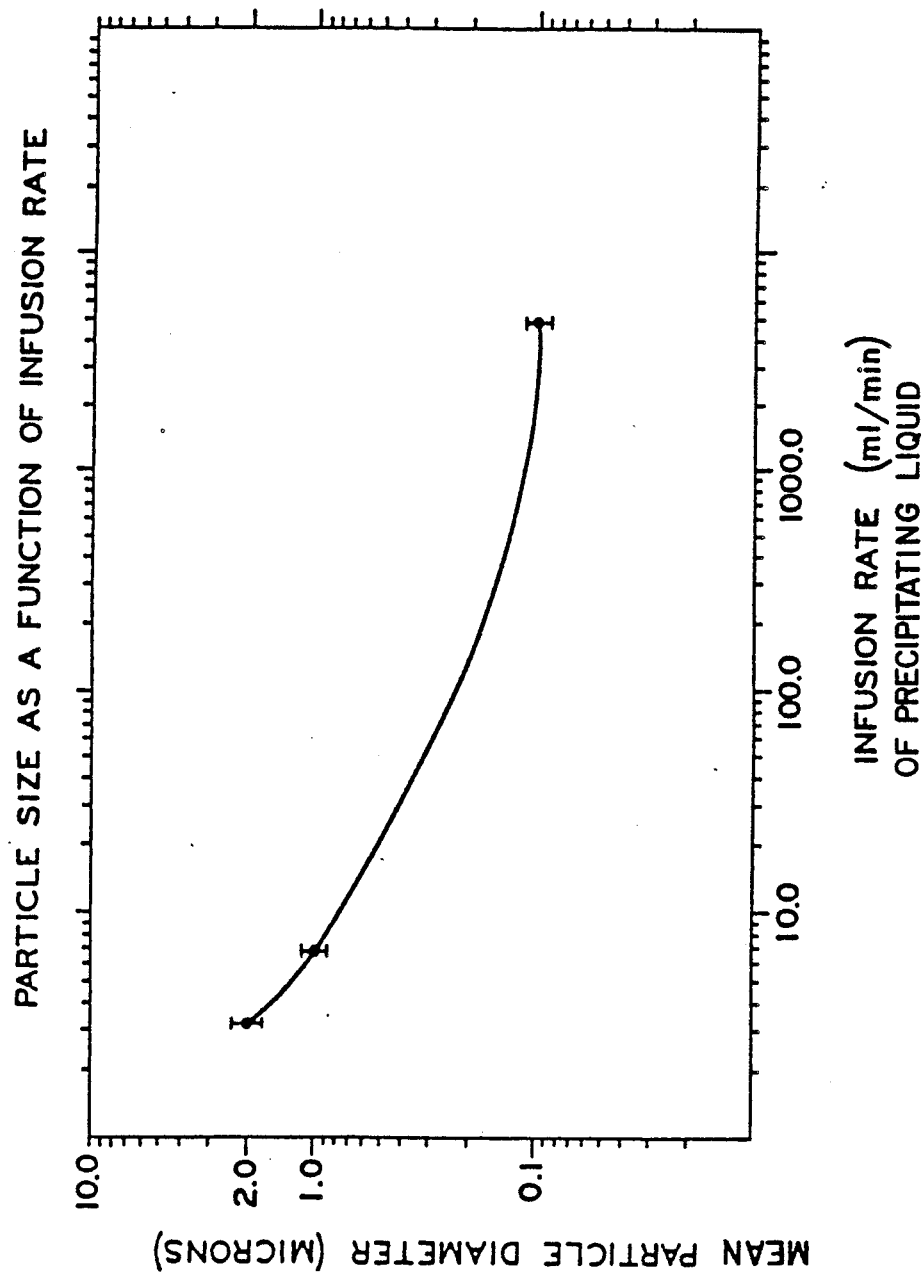
FIG. 5 is a graph demonstrating the effect on particle size of varying the infusion rate of aqueous precipitating liquid at constant temperature and stirring rate of an iodipamide ethyl ester solution.
Figure 6:
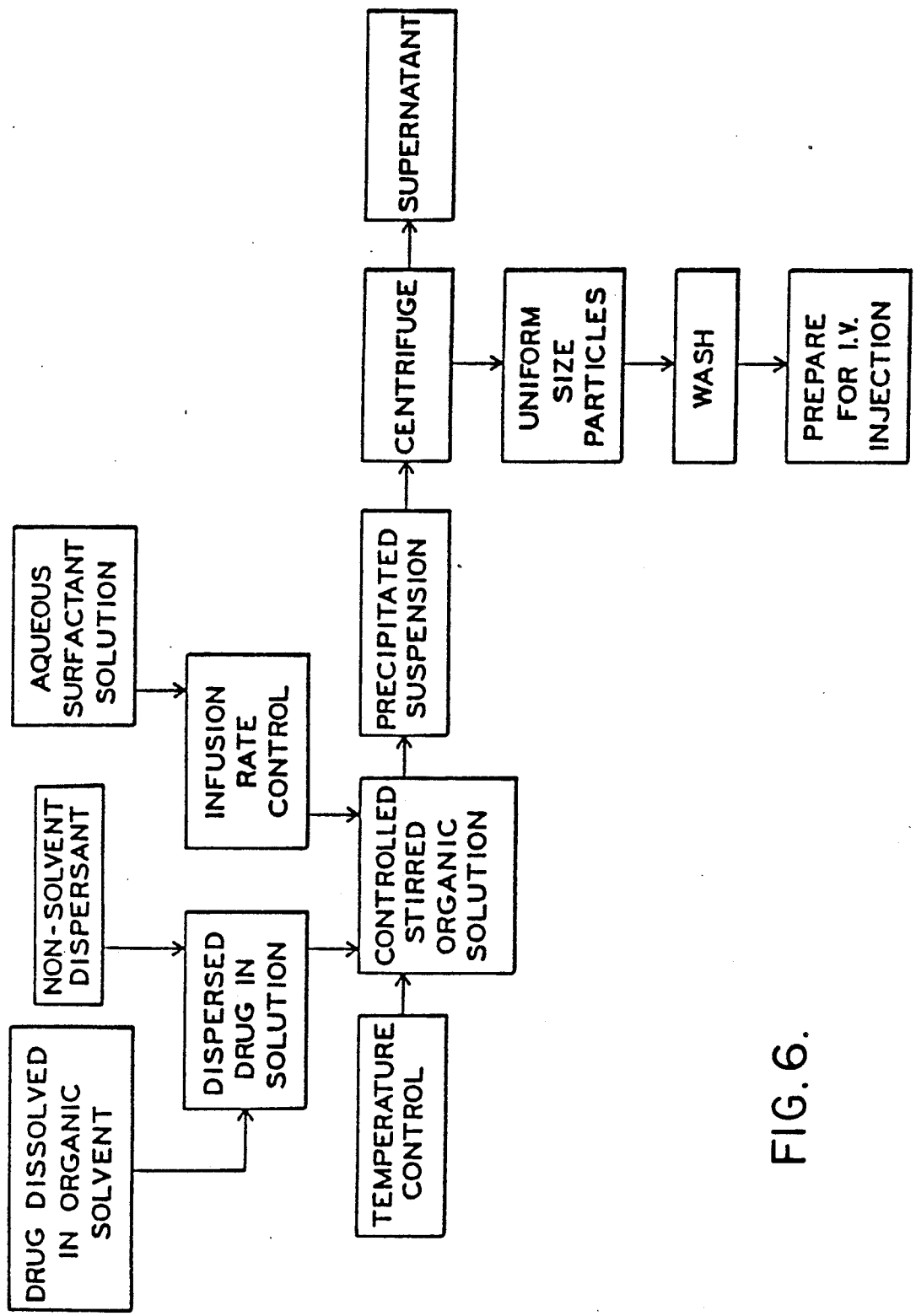
FIG. 6 is a schematic diagram of preferred steps in the inventive method.

FIGS. 3–5 show the effects on particle size of varying parameters during precipitation of IDE from a DMSO solution diluted with 1 part solution to 2 parts ethanol using an aqueous solution of 5% polyvinylpyrrolidone at different infusion rates and temperatures.

FIG. 3 shows that as the volume and stirring rate of the organic compound iodipamide ethyl ester and dimethyl sulfoxide/ethanol solution are increased, the infusion rate of aqueous surfactant solution must be increased proportionally as defined by: infusion rate (ml/min.)=23+0.14 [volume (liters)×stir rate (r.p.m.)] to produce particles of 1 micron diameter at 4° C.

FIG. 4 shows that at a constant ratio of infusion rate to [stir rate x volume], increased precipitation temperature produces larger particles.

FIG. 5 plots 3 points from the 20° C. temperature line of FIG. 3 for rate of infusion of the precipitating liquid into the organic solution to approximate the curve by which larger particles are formed from slower injection rates, showing that at a constant ratio of temperature to [stir rate×volume], particle size is inversely related to the rate of infusion of the precipitating liquid.

When FIGS. 3–5 are considered together, they show clearly that higher temperatures and slower mixing rates produce larger particles, and lower temperatures and faster mixing rates produce smaller particles. Another parameter that can be varied to affect particle size is the amount of dilution of the solution before precipitation occurs.

When the precipitation is complete, extra surfactant solution can be added to further stabilize the suspended particles against agglomeration. The extra solution can be added at a rapid rate, since essentially all the compound is now precipitated in uniformly sized particles. The precipitated particles are promptly separated from the solvent to prevent redissolving and reprecipitation of particles at undesirable sizes. Centrifuging is a preferred way to perform the separation. Other methods, including membrane filtration, reverse osmosis, and others known to persons skilled in the art may also be used to remove undesired substances. Promptly after separating the particles, the particles are washed or rinsed with normal saline solution to remove solvent and excess surfactant. Where an aqueous precipitating liquid is used, normal saline solution may be used for this purpose.

The particles prepared according to the method outlined above may be resuspended in an appropriate suspension vehicle which may be aqueous or non-aqueous solution, as the situation requires. For example where the particles formed comprise a pharmaceutical compound for parenteral administration, the particles are ultimately resuspended in an aqueous solution such as sterile water. In other instances, the particles may be suspended in a carrying agent such as an ointment, gel, or the like. Preferably, the compound has the same range of solubility in the suspension vehicle as in the precipitating liquid.

The method of the invention is illustrated by the following examples which, however, do not limit the invention as described above and set forth in the claims.

Examples 1 to 19 are presented in Table I. The solid organic compound was dissolved in the organic solvent and then diluted (except where indicated) by the non-solvent. The aqueous precipitating liquid was then infused through a needle at the given rate into the solution, at the given temperature and while stirring at the given stirring rate. The size of the particles obtained is shown for each example.

TABLE Ia

| | Example 1 | Example 2 |
|---|---|---|
| 1. solid organic compound | 10 mg 2,2',4,4',-tetra-hydroxybenzophenone | 1.4 mg RS nitrocellulose compound (¼ sec) |
| 2. organic solvent | 0.2 ml dimethyl sulfoxide | 0.2 ml dimethyl sulfoxide |
| 3. non-solvent | 0.2 ml ethanol (99%) | 0.2 ml ethanol (99%) |
| 4. aqueous precipitating liquid | 5 ml human serum albumin (0.1%) | 5 ml human serum albumin (0.1%) |
| 5. infusion rate (ml/min.) of precipitating liquid | 2.5 | 2 |
| 6. stir rate (rev./min.) of solution | 200 | 400 |
| 7. temperature of solution | 20° C. | 20° C. |
| 8. particle diameter | 0.5 micron | 0.5 micron |

TABLE Ib

| | Example 3 | Example 4 |
|---|---|---|
| 1. solid organic compound | 7 mg RS nitrocellulose (¼ sec.) | 10 mg progesterone |
| 2. organic solvent | 0.4 ml dimethyl sulfoxide | 0.2 ml dimethyl sulfoxide |
| 3. non-solvent | 0.01 ml isopropanol | 0.2 ml ethanol (99%) |
| 4. aqueous precipitating liquid | 5 ml human serum albumin (0.1%) | 5 ml human serum albumin (0.1%) |
| 5. infusion rate (ml/min.) of precipatating liquid | 2.5 | 2.5 (through an 18 gauge needle) |
| 6. stir rate (rev./min.) of solution | 200 | 400 |
| 7. temperature of solution | 20° C. | 20° C. |
| 8. particle diameter | 0.5 micron | 0.5 micron |

TABLE Ic

| | Example 5 | Example 6 |
|---|---|---|
| 1. solid organic compound | 5240 mg iosefamate ethyl ester | 10 g iothalamate ethyl ester |
| 2. organic solvent | 60 ml dimethyl sulfoxide | 32 ml dimethyl sulfoxide |
| 3. non-solvent | 20 ml ethanol (99%) | — |
| 4. aqueous precipitating liquid | 400 ml polyvinyl pyrrolidone C-15 (5%) | 800 ml polyvinyl pyrrolidone C-15 (5%) |
| 5. infusion rate (ml/min.) of precipitating liquid | 3 | 300 |
| 6. stir rate (rev./min) of solution | 200 | 300 |
| 7. temperature of solution | 20° C. | 0-2° C. initial 40° C. final |
| 8. particle diameter | 1.0 micron | 1.0 micron |

TABLE Id

| | Example 7 | Example 8 |
|---|---|---|
| 1. solid organic compound | 100 mg beta-2,3,6 triod-3-dimethyl formamidino-phenyl propionic acid ethyl ester | 100 mg beta-2,3,6 triod-3-dimethyl formamidino-phenyl propionic acid ethyl ester |
| 2. organic solvent | 2.0 ml dimethyl sulfoxide | 2.0 ml dimethyl sulfoxide |
| 3. non-solvent | 2.5 ml ethanol (99%) | 2.5 ml ethanol (99%) |
| 4. aqueous precipitating liquid | 25 ml Poloxamer 188 a poly (oxyethylene-co-oxypropylene) polymer (Pluronic F-68)(0.1%) | 25 ml human serum albumin (0.1%) |
| 5. infusion rate (ml/min.) of precipitating liquid | 750 | 750 |
| 6. stir rate (rev./min) of solution | 650 | 650 |
| 7. temperature of solution | 10° C. | 10° C. |
| 8. particle diameter | 0.1 micron | 0.1 micron |

TABLE Ie

| | Example 9 | Example 10 |
|---|---|---|
| 1. solid organic compound | 100 mg beta 2,4,6-triiod-3-dimethyl formamidino phenyl propionic acid ethyl ester | 120 mg iodipamide ethyl ester |
| 2. organic solvent | 2.0 ml dimethyl sulfoxide | 2.0 ml dimethyl sulfoxide |
| 3. non-solvent | 2.5 ml ethanol (99%) | 2.5 ml ethanol (99%) |
| 4. aqueous precipitating liquid | 25 ml polyvinyl pyrrolidone C-15 (0.1%) | 5 ml polyvinyl pyrrolidone C-15 (0.1%) |
| 5. infusion rate (ml/min.) of precipitating liquid | 750 | 300 |
| 6. stir rate (rev./min) of solution | 650 | 80 |
| 7. temperature of solution | 10° C. | 4° C. |

TABLE Ie-continued

|   | Example 9 | Example 10 |
|---|---|---|
| 8. particle diameter | 0.1 micron | 0.1 micron |

TABLE If

|   | Example 11 | Example 12 |
|---|---|---|
| 1. solid organic compound | 1200 mg iodipamide ethyl ester | 120 mg iodipamide ethyl ester |
| 2. organic solvent | 20 ml dimethyl sulfoxide | 2.0 ml dimethyl sulfoxide |
| 3. non-solvent | 25 ml ethanol (99%) | 2.5 ml ethanol (99%) |
| 4. aqueous precipitating liquid | 50 ml polyvinyl pyrrolidone C-15 (0.1%) | 5.0 ml polyvinyl pyrrolidone C-15 (0.1%) |
| 5. infusion rate (ml/min.) of precipitating liquid | 19 | 2 |
| 6. stir rate (rev./min) of solution | 190 | 200 |
| 7. temperature of solution | 10° C. | 10° C. |
| 8. particle diameter | 1.5 micron | 1.0 micron |

TABLE Ig

|   | Example 13 | Example 14 |
|---|---|---|
| 1. solid organic compound | 120 mg iodipamide ethyl ester | 10 mg isopropyl pyrrolizine derivative (NSC-278214) |
| 2. organic solvent | 2.0 ml dimethyl sulfoxide | 0.4 ml dimethyl sulfoxide |
| 3. non-solvent | 2.5 ml ethanol (99%) | — |
| 4. aqueous precipitating liquid | 25 ml poly(oxyethylene co-oxypropylene) polymer, Poloxamer 188 (Pluronic F-65) (0.1%) | 5 ml human serum albumin (0.1%) |
| 5. infusion rate (ml/min.) of precipitating liquid | 750 | 20 |
| 6. stir rate (rev./min) of solution | 700 | 300 |
| 7. temperature of solution | 0° C. | 17° C. |
| 8. particle diameter | 0.1 micron | 0.5 micron |

TABLE Ih

|   | Example 15 | Example 16 |
|---|---|---|
| 1. solid organic compound | 10 mg isopropyl pyrrolizine derivative (NSC-278214) | 10 mg isopropyl pyrrolizine derivative (NSC-278214) |
| 2. organic solvent | 0.4 ml N,N'-dimethyl acetamide | 0.4 ml dimethyl sulfoxide |
| 3. non-solvent | — | 0.2 ml ethanol (99%) |
| 4. aqueous precipitating liquid | 20 ml human serum albumin (0.1%) | 20 ml human serum albumin (0.1%) |
| 5. infusion rate (ml/min.) of precipitating liquid | 38 | 100 |
| 6. stir rate (rev./min) of solution | 50 | 200 |
| 7. temperature of solution | 0° C. | 0° C. |
| 8. particle diameter | 0.5 micron | 0.1 micron |

TABLE Ii

|   | Example 17 | Example 18 |
|---|---|---|
| 1. solid organic compound | 1.5 mg. 1,2 diaminocyclohexane malinate platinum (II) | 10 mg N-(trifluoroacetyl) adriomycin 14 valerate |
| 2. organic solvent | 0.05 ml phenol | 0.2 ml dimethyl sulfoxide |
| 3. non-solvent | 0.45 ml m-aminophenol and 0.25 ml ethanol (99%) | 0.2 ml ethanol (99%) |
| 4. aqueous precipitating liquid | 5 ml human serum albumin (0.1%) | 5 ml human serum albumin (0.1%) |
| 5. infusion rate (ml/min.) of precipitating liquid | 5 | 2.5 |
| 6. stir rate (rev./min) of solution | 200 | 200 |
| 7. temperature of solution | 20° C. | 20° C. |
| 8. particle diameter | 0.1 micron | 1.0 micron |

TABLE Ij

|   | Example 19 | Example 20 |
|---|---|---|
| 1. solid organic compound | 200 mg heparin-benzalkonium chloride complex | 10 mg organic compound* (see list) |
| 2. organic solvent | 10 ml isopropanol | 0.2 ml dimethyl sulfoxide |
| 3. non-solvent | — | 0.2 ml ethanol (99%) |
| 4. aqueous precipitating liquid | 200 ml water | 5 ml human serum albumin (0.1%) |
| 5. infusion rate (ml/min.) of precipitating liquid | 3.7 | 2.5 |
| 6. stir rate (rev./min) of solution | 300 | 250 |
| 7. temperature of solution | 20° C. | 20° C. |
| 8. particle diameter | 0.5 micron | 1.0 micron |

*norethisterone, acetyl salicylic acid, wafarin, heparin-tridodecyl methyl ammonium chloride complex, sulfamethoxazole, cephalexin, prednisolone acetate, diazepam, methidone, naloxone, disulfiram, mercaptopurine, digitoxin, primaquine, mefloquine, atropine, scopolamine, thiazide, furosemide, propanelol, methyl methacrylate, poly methyl methacrylate, 5-fluorodeoxyuridine, cytosine arabinoside, acyclovir, levonorgestrel Examples 1 to 19 show how the process can be used to produce aqueous dispersions of a wide variety of compounds that have low aqueous solubility and for which particle size can be controlled with substantial precision and predictability. Conditions would be varied from compound to compound according to the invention in order to optimize results. This may in some cases include chemical modification of the compound to achieve the desired solubility.

Because of the range of examples presented above, it is reasonable to one skilled in the art, that numerous other compounds would be expected to behave in similar fashion.

Example 20 is also presented in Table I. This example should be performed in the same manner as examples 1 to 19, and would make particles of the listed compounds within the scope of the invention.

Examples 21 to 28 are presented in Table II. In each example, the given quantity of iodipamide ethyl ester was dissolved in the given volume of dimethyl sulfoxide, then diluted with the given volume of ethanol. The aqueous precipitating liquid was prepared from polyvinylpyrrolidone then infused at the given infusion rate through a needle with the given gauge into the solution while the solution was stirred at the given stir rate. The precipitation was carried out in the given vessel at the given temperature. After precipitation, the given amount of saline was added to further stabilize the dispersion. In each example, the mean particle diameter was about 1.0 micron and substantially uniform.

TABLE IIa

Parameters for Iodipamide Ethyl Ester Particle Precipitation

| Material | Example 21 0.5 gm | Example 22 1 gm | Example 23 2 gm |
|---|---|---|---|
| iodipamide ethyl ester (60 mg/ml) | 10 ml | 20 ml | 40 ml |
| ethanol (99%) | 12.5 ml | 25 ml | 50 ml |
| polyvinyl pyrrolidone | 25 ml | 50 ml | 100 ml |
| 0.9% saline | 15 ml | 30 ml | 60 ml |
| stir rate | 125 rpm | 190 rpm | 300 rpm |
| temperature | 4° C. | 4° C. | 4° C. |
| infusion rate | 11 ml/min | 19 ml/min | 30 ml/min |
| infusion needle size | 19 g | 19 g | 19 g |
| S.B. length | 1.5" | 1.5" | 1.5" |
| vessel diam. | 2.38" | 2.38" | 2.38" |
| vessel | 250 ml polypropylene bottle | 250 ml polypropylene bottle | 250 ml polypropylene breaker |

TABLE IIb

Parameters for Iodipamide Ethyl Ester Particle Precipitation

| Material | Example 24 3.5 gm | Example 25 5 gm | Example 26 10 gm |
|---|---|---|---|
| iodipamide ethyl ester (60 mg/ml) | 70 ml | 100 ml | 200 ml |
| ethanol (99%) | 87.5 ml | 125 ml | 250 ml |
| polyvinyl pyrrolidone | 175 ml | 250 ml | 500 ml |
| 0.9% saline | 105 ml | 150 ml | 300 ml |
| stir rate | 330 rpm | 200 rpm | 300 rpm |
| temperature | — | — | — |
| infusion rate | 45 ml/min | 60 ml/min | 85 ml/min |
| infusion needle size | 19 g | 18 g | 18 g |
| S.B. length | 1.88" | 2.75" | 2.75" |
| vessel diam. | 3.38" | 5.0" | 5.0" |
| vessel | 1,000 ml glass beaker | 2,000 ml glass beaker | 2,000 ml glass |

TABLE IIc

Parameters for Iodipamide Ethyl Ester Particle Precipitation

| Material | Example 27 20 gm | Example 28 40 gm |
|---|---|---|
| iodipamide ethyl ester (60 mg/ml) | 400 ml | 800 ml |
| ethanol (99%) | 500 ml | 1,000 ml |
| polyvinyl pyrrolidone | 1,000 ml | 2,000 ml |
| 0.9% saline | 600 ml | 1,200 ml |
| stir rate | 175 rpm | 210 rpm |
| temperature | — | — |
| infusion rate | 120 ml/min | 175 ml/min |
| infusion needle size | 16 g | 16 g |
| S.B. length | 3.25" | 3.25" |
| vessel diam. | 8.6" | 8.6" |
| vessel | 9 L Bellco vessel | 9 L Bellco vessel |

EXAMPLE 29

Preparation of Iodipamide Ethyl Ester Particles for Administration to a Patient.

Particles of iodipamide ethyl ester (IDE) with a size of about 1 micron may be prepared for administration to a patient. IDE is the water-insoluble ethyl ester of iodipamide, a water-soluble radiopaque compound used clinically for radiographic examination of the gallbladder. The synthesis of iodipamide ethyl ester is known in the art (for example, esterification by alcohol and acid or by a Schotten-Bauman reaction).

IDE is only minimally soluble in water ($10^{-5}$ M) and can be precipitated easily from the dimethyl sulfoxide (DMSO)/ethanol solvent mixture. However, the simple addition of water to this solution results in IDE particles with extremely rough contours; these particles vary in size from less than one micron to greater than 300 microns in diameter. In light of the problems that rough contours could damage vascular endothelial cells and promote aggregation, and that large particles could create pulmonary emboli, the method of this invention provides a more refined procedure for controlling particle size and shape.

Particle Precipitation Procedure. Physical methods for modifying and controlling particle size, such as ball milling, grinding or sonication result in preparations with a very broad range of particle diameters. These methods are commonly used to eliminate large particles (greater than 4–5 microns) which could embolize in the pulmonary capillary bed, but generally some particles of submicron size are also produced; these very small particles have been shown to be more toxic than 1–2 micron particles, possibly due to increased protein binding resulting from the much larger surface area inherent with particles of smaller diameters, or possibly because of excessive uptake by bone marrow cells.

A chemical precipitation procedure for producing particles of a given size was developed to avoid these problems. By adding an aqueous solution of polyvinylpyrrolidone, at controlled rates and temperatures, to IDE dissolved in a dimethyl sulfoxide/ethanol solvent, apparently spherical, amorphous particles can be produced with an extremely narrow size distribution. For a particle preparation with a mean diameter of 1 micron, the total range of particle diameters is 0.4 to 2.0 microns with 90 per cent of the particles ranging in size between 0.5 and 1.5 microns, as determined by microscopy.

By carefully controlling precipitation parameters, particle preparations demonstrating different mean diameters, but with a similarly small range of diameters, can be produced.

The IDE particles produced using this methodology are stable in whole blood with little apparent tendency toward aggregation. When suspended in whole blood, there is essentially no tendency for one micron IDE particles to aggregate with themselves or with formed elements of blood. The IDE particles have smooth contours.

EXAMPLE 30

Preparation of Uniformly-Sized Particles from Inorganic Compounds

A 10% solution of aluminum chloride hexahydrate ($AlCl_3.6H_2O$) is prepared by adding 1 gram of this compound to 10 ml of 99% ethanol. This mixture is heated to approximately 50° C. until substantially all of the $AlCl_3.6H_2O$ is dissolved. The solution was then allowed to cool to room temperature. Subsequently, 5 ml of acetone is added to 2.5 ml of $AlCl_3.6H_2O$/ethanol solution in 25 ml beaker and cooled to 4° C. This solution is stirred rapidly using a magnetic stirrer.

Next, 5 ml of 0.5% aqueous polyvinylpyrrolidone (PVP) is infused into the solution at pH 5 at a rate of 114 ml/minute. Immediately after the infusion, the solution becomes hazy as particles of $AlCl_3.6H_2O$ are formed. Examination under a microscope (400×) reveals the presence of small spherical, monodispersed particles. The suspension is then centrifuged at 10,000 RPM for 15 minute and the pellet is resuspended in aqueous 0.1% PVP/0.9% NaCl solution. Laser light scattering analysis of this suspension reveals a mean particle diameter of 285 nm.

EXAMPLE 31

Preparation of Uniformly-Spaced Particles in Non-Aqueous Media

Mitindomide, a pharmaceutical intended for parenteral administration, has a solubility in water of 70 ug/ml at room temperature. Although this normally is considered to be water-insoluble, we encountered significant yield loss when we precipitate and wash with an aqueous solution. The solubility of mitindomide in absolute ethanol is less than 4 ug/ml at room temperature. This solubility difference between water and ethanol, although small, is significant when one is concerned with manufacturing yields. Therefore, a procedure was developed for preparing mitinodomide particles in ethanol. The final suspension is prepared in aqueous medium. However, most of the preparation involves non-aqueous solvents.

A mitindomide solution of 30 mg/ml in DMSO is prepared and filtered through an 0.2 micron nylon filter immediately prior to use. A 1% (w/v) polyvinylpyrrolidone (PVP) solution in 99% ethanol is prepared and filtered through an 0.2 micron filter immediately prior to use. The mitindomide particles are prepared by mixing the 1% PVP/ethanol solution at a rate of six (6) liters/minute with the mitindomide/DMSO solution at a rate of 250 ml/minute at a temperature of 0° C. After 90 minutes of recirculation at this temperature, laser light scattering analysis reveals a mean particle diameter of approximately 400 nm.

At this stage the suspension can be transferred to a 500 ml bottle for storage at −20° C. until further processing is desired or one may proceed directly to the following procedures.

Before use, the suspension must be washed to remove DMSO. This is accomplished by centrifugation, filtration or by any other means known to one skilled in the art. The wash fluid can be water. However, to maximize yield, it is preferred to wash with the 99% ethanol.

After washing the particles may be resuspended in ethanol and stored at −20° C.

When the suspension is to be prepared in final form, the suspension is centrifuged and the separated mitindomide particles are resuspended in aqueous PVP solution. This suspension vehicle may contain other additives such as buffer, preservatives, or other excipients as may be deemed necessary. The resultant "concentrated" suspension is then lyophilized to remove the ethanol and most of the water. The lyophil can be reconstituted by adding sterile water just prior to use.

The examples provided above are not meant to be exclusive. Many other variations of the present invention would be obvious to those skilled in the art and are contemplated to be within the scope of the appended claims.

We claim:

1. A method of making uniformly sized particles of a solid compound having an aqueous solubility from about one part per ten thousand to about one part per one hundred, comprising:
   (a) preparing a solution of the solid compound in a suitable solvent for the compound wherein the solubility of the compound in the solvent is greater than about 10 mg/ml;
   (b) infusing a substantially non-aqueous precipitating liquid into the solution at a temperature between about −50° C. and at an infusion rate of from about 0.01 ml per min. to about 3000 ml per min. per 50 ml unit volume of solution, the solid compound having essentially little solubility in the precipitating liquid and the solvent being miscible in the precipitating liquid, so as to produce a suspension of precipitated amorphous, non-crystalline solid compound in the form of substantially non-aggregated particles of a uniform size selected from a particle diameter range of up to about 10 microns, the particle size being directly related to the solution temperature during precipitation and inversely related to the infusion rate; and
   (c) separating the particles from the solvent and washing in a suitable substantially non-aqueous washing liquid, said particles having essentially little solubility in said washing liquid.

2. The method according to claim 1, wherein additional precipitating liquid is added to the suspension before the particles are separated.

3. The method according to claim 1, wherein the particles are separated by centrifugation, membrane filtration, or reverse osmosis.

4. The method according to claim 1, wherein the washing liquid is the same as the precipitating liquid.

5. The method according to claim 1, wherein the precipitating liquid is a surfactant solution.

6. The method according to claim 1, wherein the solution is prepared such that the concentration of the solid compound is near its solubility limit in the solvent.

7. The method according to claim 1, wherein the solvent is an organic solvent selected from the group consisting of dimethyl sulfoxide, dimethyl formamide, N,N'-dimethyl acetamide, phenol, isopropanol, ethanol and tetrahydrofuran.

8. The method according to claim 1, wherein the solid compound is mitindomide, the solvent is DMSO, and the precipitating liquid is a 1% (w/v) polyvinylpyrrolidone in 99% ethanol.

9. The method according to claim 1, wherein the step infusing the precipitating liquid is carried out by means of a needle of standard gauge.

10. The method according to claim 1, wherein the mean particle diameter is selected from the range of from about 0.01 micron to about 0.1 micron.

11. The method according to claim 1, wherein the mean particle diameter is selected from the range of from about 0.1 to about 4 microns.

12. The method according to claim 1, wherein the mean particle diameter is from about 1 to about 10 microns.

13. The method according to claim 1 wherein the particle size distribution has a maximum relative standard deviation of 30 percent.

14. The method according to claim 1 wherein the precipitating liquid is infused into a stream of the solution.

15. The method according to claim 1, further comprising, before step (b), the step of measuring the zeta potential of the solid compound and using the zeta potential to select a surfactant and to determine the amount of surfactant in the precipitating liquid which is required to prevent aggregation of particles.

16. The method according to claim 1, wherein the particles are resuspended in a suspending liquid which is pharmaceutically acceptable for injection into a patient.

17. A method of making uniformly sized particles of a solid compound having an organic solubility from less than about one part per ten thousand, comprising:
  (a) preparing a solution of the solid compound in an aqueous solvent for the compound, wherein the solubility of the compound in the solvent is greater than about 10 mg/ml;
  (b) infusing a substantially non-aqueous precipitating liquid into the solution at a temperature between about −50° C. and about 100° C. and at an infusion rate of from about 0.01 ml per min. to about 3000 ml per min. per 50 ml unit volume of solution, the solid compound having essentially little solubility in the precipitating liquid and the solvent being miscible in the precipitating liquid, so as to produce a suspension of precipitated amorphous, non-crystalline solid compound in the form of substantially non-aggregated particles of a uniform size selected from a particle of diameter range of up to about 10 microns, the particle size being directly related to the solution temperature during precipitation and inversely related to the infusion rate; and
  (c) separating the particles from the solvent and washing in a substantially non-aqueous washing liquid, said particles having essentially little solubility in said washing liquid.

18. The method according to claim 17, wherein the precipitating liquid comprises a surfactant solution.

19. A method of making uniformly sized particles of a solid inorganic compound, comprising:
  (a) preparing a solution of the compound in a water-miscible solvent for the compounds, wherein the solubility of the compound in the solvent is greater than about 10 mg/ml;
  (b) infusing an aqueous precipitating liquid into the solution at a temperature between about −50° C. and about 100° C. and at an infusion rate of from about 0.01 ml per min. to about 3000 ml per min. per 50 ml unit volume of solution, the solid compound having essentially little solubility in the precipitating liquid and the solvent being miscible in the precipitating liquid, so as to produce a suspension of precipitated amorphous, non-crystalline solid compound in the form of substantially non-aggregated particles of a uniform size selected from a particle diameter range of up to about 10 microns, the particle size being directly related to the solution temperature during precipitation and inversely related to the infusion rate; and
  (c) separating the particles from the solvent and washing in aqueous washing liquid, said particles having essentially little solubility in said washing liquid.

20. The method according to claim 19, wherein the precipitating liquid comprises a surfactant solution.

21. The method according to claim 19, wherein the precipitating liquid is a surfactant solution selected from the group consisting of 5% polyvinylpyrrolidone in water, 0.1% polyvinylpyrrolidone in water, 0.1% human serum albumin in water, 0.1% of a poly (oxyethylene-co-oxypropylene) polymer with average molecular weight of 8350 formed by addition of propylene oxide to the two hydroxyl groups of a propylene glycol initiator, 0.33% gelatin in water, 0.33% gelatin and 0.6% hetastarch in water, 0.33% gelatin and 0.02% propylene glycol in water, and 0.33% gelatin and 2% sucrose in water.

22. The method according to claim 21, wherein the solid compound is aluminum chloride hexahydrate, the solvent is ethanol, and the precipitating liquid is a 0.5% aqueous polyvinylpyrrolidone solution.

* * * * *

UNITED STATES PATENT AND TRADEMARK OFFICE
CERTIFICATE OF CORRECTION

PATENT NO. : 4,997,454
DATED : Mar. 5, 1991
INVENTOR(S) : MICHAEL R. VIOLANTE, et al

It is certified that error appears in the above-identified patent and that said Letters Patent is hereby corrected as shown below:

```
 Title page, [63], change "1989" to -1985-
Column 2, line 53 change "With" to -with-
Column 2, line 64 change "first" to -first,-
Column 4, line 14 change "triiodobenzoio" to -triiodobenzoic-
Column 10, line 51 change "triiod" to -triod-
Column 12, line 54 change "pam, methidone," to -pam, clonazepam,
    methidone-
Column 13, line 38 change "breaker" to -beaker-
Column 13, lines 56 and 57 change "glass" to -glass beaker-
Column 15, line 46 change "mitinodomide" to -mitindomide-
Column 16, line 26 change "compound" to -compound,-
Column 16, line 31 change "C. and" to -C. and about 100®C. and-
Column 17, line 3 change "step" to -step of-
Column 18, line 12 change "compounds," to -compound,-
```

Signed and Sealed this

First Day of June, 1993

Attest:

MICHAEL K. KIRK

*Attesting Officer*   *Acting Commissioner of Patents and Trademarks*